United States Patent [19]

D'Angelo et al.

[11] Patent Number: 4,749,797

[45] Date of Patent: Jun. 7, 1988

[54] TETRA-ALKYL-2,2,5,5-CYCLOHEXANONE-4-OL-1 COMPOUNDS AND THEIR SULPHONYL DERIVATIVES, THE PROCESS AND THE INTERMEDIATES FOR PREPARING THEM AND THEIR USE IN THE SYNTHESIS OF CIS-CYCLOPROPANE LACTONES

[75] Inventors: Jean D'Angelo, Massy; Gilbert Revial, Paris; Robert Azerad, Ris Orangis; Didier Buisson, Maintenon, all of France

[73] Assignee: Roussel Uclaf, Paris, France

[21] Appl. No.: 878,039

[22] Filed: Jun. 24, 1986

Related U.S. Application Data

[62] Division of Ser. No. 691,525, Dec. 5, 1984, Pat. No. 4,610,826.

[30] Foreign Application Priority Data

Apr. 8, 1983 [FR] France .................. 83 05772

[51] Int. Cl.[4] .................. C07D 311/94; C07D 313/04
[52] U.S. Cl. .................. 549/283; 549/271; 558/44; 568/376; 435/148; 435/911; 435/917; 435/929; 435/931; 435/935; 435/939
[58] Field of Search .............. 568/376; 549/283, 290; 562/506

[56] References Cited

U.S. PATENT DOCUMENTS 3,418,290 12/1968 Bantjes .................. 549/271
3,728,372 4/1973 Siddoll .................. 558/44
4,072,715 2/1978 Boguth et al. .................. 568/376

FOREIGN PATENT DOCUMENTS 0032471 3/1979 Japan .................. 549/283

OTHER PUBLICATIONS

Conia, "Alkylation of Saturated and, etc." CA 430h: 1963.
Nelson et al., "Bicyclo[3.1.0]hexane, etc.", JOC 22 (1957) 1146.

Primary Examiner—Glennon H. Hollrah
Assistant Examiner—Patricia L. Morris
Attorney, Agent, or Firm—Bierman & Muserlian

[57] ABSTRACT

New tetra-alkyl-2,2,5,5-cyclohexanone-4-ol-1-compounds and their sulphonyl derivatives with the general formula:

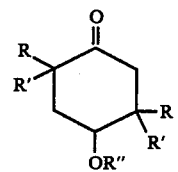

in which:
each of R and R', identical or different, represents an alkyl radical (1–5 carbons) and R" represents a hydrogen atom or a radical $SO_2R'''$ in which R''' represents an alkyl radical (1–5 carbons) or an aryl radical (6–14 carbons), the process and the intermediates for their preparation, as well as their use in the synthesis of cyclopropane lactones of cis structure.

10 Claims, No Drawings

TETRA-ALKYL-2,2,5,5-CYCLOHEXANONE-4-OL-1 COMPOUNDS AND THEIR SULPHONYL DERIVATIVES, THE PROCESS AND THE INTERMEDIATES FOR PREPARING THEM AND THEIR USE IN THE SYNTHESIS OF CIS-CYCLOPROPANE LACTONES

This is a division of Ser. No. 691,525 filed Dec. 5, 1984 now U.S. Pat. No. 4,610,826.

The present invention has as its subject new tetra-alkyl-2,2,5,5-cyclohexanone-4-ol-1 compounds and their sulphonyl derivatives, the process and the intermediates for their preparation and their use in the synthesis of cyclopropane lactones of cis structure.

The present invention thus has as its subject the tetra-alkyl-2,2,5,5-cyclohexanone-4-ol-1 compounds and their sulphonyl derivatives with the general formula (I):

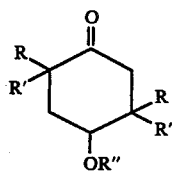

(I)

in which:
each of R and R', identical or different, represents an alkyl radical having from 1 to 5 carbon atoms and R" represents a hydrogen atom or a radical —SO$_2$R'" in which R'" represents an alkyl radical containing from 1 to 5 carbon atoms or an aryl radical containing from 6 to 14 carbon atoms.

In the general formula (I), each of R and R' preferably represents a methyl, ethyl or propyl radical, and when R" represents a radical —SO$_2$R'", R'" preferably represents a methyl, ethyl, phenyl, p-tolyl or xylyl radical.

Among the compounds with the general formula (I), the invention notably has as its subject those in which R and R' are identical and each represents a methyl radical.

Among the compounds with the general formula (I), the invention also has particularly as its subject those in which R" represents a hydrogen atom and those in which R" represents a radical —SO$_2$R'", in which R'" represents a methyl or p-tolyl radical.

Among the compounds with the general formula (I), the invention has more particularly as its subject those in which the configuration of the carbon atom carrying the OR" group is (S).

The subject of the invention is also a process for the preparation of the compounds with the formula (I), as previously defined, characterized in that the cyclohexanedione-1,4 with the formula (II):

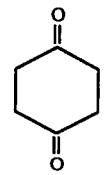

(II)

is alkylated in order to obtain the tetra-alkyl-2,2,5,5-cyclohexanedione-1,4 compounds with the formula (III):

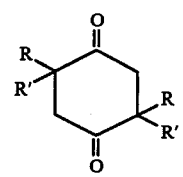

(III)

which are reduced selectively so as to obtain the corresponding tetra-alkyl-2,2,5,5-cyclohexanone-4-ol-1 compounds, with the formula (I), in which R" represents a hydrogen atom, and that, if desired, the said products are converted into the corresponding sulphonyl derivatives, with the formula (I), in which R" represents an —SO$_2$—R'" radical, as previously defined.

In the preferential conditions for carring out the alkylation stage of the invention process:
if the radicals R and R' are identical, the tetra-alkylation reaction can be carried out in a single stage, starting from cyclohexanedione-1,4, and with an alkyl halide in an anhydrous medium, in tetrahydrofuran in the presence of an alkaline alcoholate:
if the radicals R and R' are different, but also if they are identical, the alkylation reaction is carried out in two stages, starting with ethylcyclohexanedione-1,4-dicarboxylate-2,5 in the same conditions as those described above for the tetra-alkylation of cyclohexanedione-1,4.

This stage of alkylation can be illustrated by the following reactional scheme:

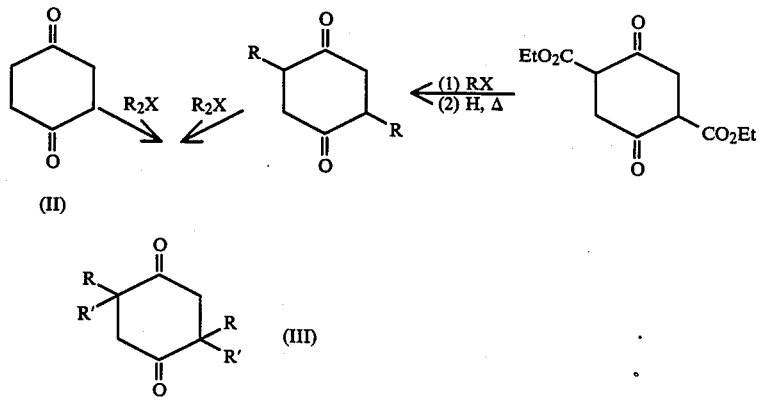

R$_2$ may be R or R',

X=halogen (Cl, Br or I).

The starting cyclohexanedione-1,4 (II) is a compound easily obtainable by reducing hydroquinone.

In the preferential conditions of carrying out the selective reduction stage of the invention process, a monoenolate of the compound with the formula (III) is formed first of all by means of an alkaline alcoholate. It is preferred to work in an anhydrous medium, in tetrahydrofuran and at a temperature near to 0° C.

As alkaline alcoholate, there can be used a sodium alcoholate of a lower aliphatic alcohol, having from 1 to 6 carbon atoms, preferably sodium tert-butylate or sodium tert-amulate.

The selective reduction itself is preferably carried out by means of a hydride such as diisobutylaluminium hydride or a borohydride, such as sodium borohydride.

In the conditions most preferred for carrying out the selective reduction stage of the invention process, the said reduction is carried out by microbiological means, particularly by means of a fungi imperfecti, chosen notably from the group constituted by Curvularia, Aspergillus, Mucor, Geotrichum, Penicillium, Rhizopus, Kloeckera, Cunninghamella, Cylindrocarpon, Fusarium, Neurospora and Trichothecium.

Using the above micro-organisms offers the very important advantage of leading to a selective and stereospecific reduction of the diketone compound into a ketol of (S) configuration.

Among the above micro-organisms, those chosen from the group constituted by *Curvularia lunata, Aspergillus niger, Aspergillus ochraceus, Mucor racemosus* and *Penicilium chrysogenum* are quite particularly preferred for the degree of selectivity and stereo-specificity which they enable to be attained.

The sulphonylation stage of the invention process is preferably carried out by means of a halide of an alkyl or aryl sulphonic acid, and more particularly, by means of mesyl chloride or tolyl chloride, while operating in an anhydrous medium, in the presence of a base and and a temperature near to 0° C.

The compounds with the formula (III), as previously defined, are new products. As such, the compounds with the formula (III), and particularly those in which R and R' are identical and each represents a methyl radical, constitute one of the subjects of the invention.

Furthermore, the invention has as its subject, a use of the compounds with the formula (I) as defined in claim 1, characterized in that, if required, the compounds with the formula (I) in which R" represents a hydrogen atom, are converted into sulphonyl derivatives, that the said sulphonyl derivatives are oxidized by means of a peracid into lactones with the formula (IV):

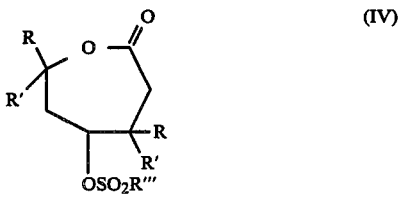

that a cyclopropanation of the said lactones (IV) is then carried out in a basic medium so as to obtain the corresponding cyclopropane lactones of cis structure, answering to the general formula (V):

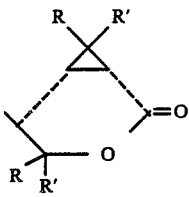

The oxidizing reaction of the sulphonyl derivatives can be carried out by means of a peracid such as perbenzoic acid, monoperphthalic acid, peracetic acid, metachloroperbenzoic acid or trifluoroperacetic acid, but preferably in the presence of metachloroperbenzoic acid, in an anhydrous medium, preferably in a halogenated hydrocarbide such as dichloromethane, at ambient temperature, and over a time period of between 10 and 100 hours.

The last stage of the use according to the invention consists in effecting the intra-molecular cyclization of the sulphonated lactone (IV) into cis-cyclopropane lactone with the formula (V). This cyclization is preferably carried out in the presence of an alkaline alcoholate, in an anhydrous medium, preferably in tetrahydrofuran, at a temperature of about 0° C.

The invention has particularly as its subject a use as previously defined, characterized in that R and R' are identical and each represents a methyl radical.

The alkaline alcoholate utilized above can notably be one of those which has previously been cited for the formation of the mono-enolate of the compound with the formula (III).

The compounds with the formula (IV), as previously defined, are new products. As such, the said compounds with the formula (IV), notably those in which R and R' are identical and each represents a methyl radical, and quite particularly, those in which the configuration of the carbon atom carrying the sulphonyl group is (S), that is to say, the lactone of (S) trimethyl-3,3,6-hydroxy-6-mesyloxy-4-heptanoic acid, constitute one of the subjects of the invention.

The cyclopropane lactones with the formula (V) constitute particularly valuable intermediates in the synthesis of substituted cis-cyclopropane carboxylic acids, notably in the synthesis of cis-chrysanthemic acid or cis-dimethyl-2,2-(methyl-2'-propenyl-1')-3-cyclopropane-1-carboxylic acid, of which there are known, on the one hand, the notably insecticidal or olfactory properties of certain of its esters, and on the other hand, the interest as intermediates in the synthesis of other esters of cyclopropane carboxylic dihalogenovinylic acids, which also possess remarkable insecticidal properties.

Cis-chrysanthemic (1R,3S) acid thus constitutes a particularly important intermediate in the synthesis of deltamethrine, discovered by M. ELLIOTT in 1974, this compound allying exceptional insecticidal properties with a reduced toxicity towards the higher organisms and a weak persistance in the natural environment.

This (1R,1S) cis-chrysanthenic acid can therefore be obtained, starting with the lactone with the formula (V) of (1R,3S) configuration in which R and R' are identical and each represents a methyl radical, itself obtained by starting with the corresponding lactone with the formula (IV), of (4S) configuration.

The lactone of cis-dimethyl-2,2-(methyl-2'-propenyl-1')-3-cyclopropane-1-carboxylic acid, or the lactone of cis-chrysanthemic acid with the formula (V) in which R=R'=—CH₃ has already been described in the French Pat. No. 69.05865, as an intermediate in the preparation of racemic cis-chrysanthemic acid, this lactone itself being obtained by a suite of stages, starting from trans-chrysanthemic acid.

Because the cyclopropane lactones with the formula (V) constitute particularly valuable intermediates in the synthesis of cyclopropane carboxylic acids substituted in position 3 by a branched vinyl chain, the present Application is particularly interesting from an industrial view-point, to the extent that it describes the preparation of the said lactones in few stages, starting with easily accessible products and with particularly simple operating conditions, and at small energy cost.

Furthermore, the intermediates obtained are for the most part presented in the form of crystallized products, which greatly simplifies their purification when this proves to be necessary.

The following examples enable the invention to be illustrated, without however, conferring any limitation on it.

EXAMPLE 1

Tetramethyl-2,2,5,5-cyclohexanone-4-ol-1

Stage A: Tetramethyl-2,2,5,5-cyclohexanedione-1,4

106 ml of a 1.5M solution of sodium tert-amylate in benzene is added drop by drop, over one hour, to 4.48 g of cyclohexanedione-1,4 and 10.2 ml of methyl iodide in solution in 100 ml of anhydrous tetrahydrofuran at 0° C. When the addition is finished, the solution is agitated at 20° C. for one hour.

After hydrolyzing by the addition of water and separation, the aqueous phase is extracted with ether. The organic phases are combined, then washed with water and dried. After evaporating, 3.25 g of the expected compound is isolated by chromatography on a silica column (eluent: ethyl acetate-hexane 20/80) and crystallization from hexane. Yield: 50%

Melting point: 112° C.
IR Spectrum (Nujol): 1700 cm⁻¹.
NMR ¹H Spectrum (60 MHz, CCl₄): 2.5 (s 4H) 1.1 (s 12H).

Stage A': Tetramethyl-2,2,5,5-cyclohexanedione-1,4

Step 1:

(a) 13.7 ml of methyl iodide is added to 25.6 g of ethyl cyclohexanedione-1,4-dicarboxylate-2,5 and 10.4 g of sodium hydroxide in solution in a mixture of 200 ml of 95° ethyl alcohol and 50 ml of water at 0° C., under agitation. The solution obtained is then kept at 25° C. for 100 hours. After evaporation of the solvent, the residue is taken up with water, then extracted with ether. The ethereal solution is washed with salt water and dried. After evaporation, 24 g of crude oil is obtained.

(b) The 24 g of the product obtained above is then agitated in 200 ml of 20% perchloric acid at 100° C. for two hours thirty minutes. After extraction with methylene chloride and evaporation, the crude product is chromatographed on a silica column, (eluent: ethyl acetate-hexane 40/60). 8.5 g of dimethyl-2,5-cyclohexanedione-1,4 is obtained (mixture of 2 diastereo-isomers).

IR spectrum (film): 1700 cm⁻¹.
NMR ¹H spectrum (60 MHz, CCl₄): 3.0–2.2 (m 6H) 1.1 (dJ-6 Hz 6H).

Step 2:

28 ml of a 1.5M solution of sodium tert-amylate in benzene is added at 0° C. and over 15 minutes to 3 g of dimethyl-2,5-cyclohexanedione-1,4 and 2.6 ml of methyl iodide in solution in 30 ml of anhydrous tetrahydrofuran. After hydrolyzing with water and separation, the aqueous phase is extracted with ether. The organic phases are combined, then washed with water and dried. After evaporation and purification by chromatography on a silica column (eluent: ethyl acetate-hexane 20/80), 2.9 g of tetramethyl-2,2,5,5-cyclohexanedione-1,4 is obtained, (yield 82%), which presents the same characteristics as the dione obtained according to example 1.

Stage B: Tetramethyl-2,2,5,5-cyclohexanone-4-ol-1

8 ml of a 1,5M solution of sodium tert-amylate in benzene is added drop by drop at −20° C. to 2 g of tetramethyl-2,2,5,5-cyclohexanedione-1,4, agitated in 12 ml of anhydrous tetrahydrofuran. The solution obtained is maintained for one hour at 0° C., then the mixture is again taken to −20° C., and 24 ml of a 1M solution of diisobutyl aluminium hydride in hexane is added drop by drop. After 30 minutes at this temperature, there are successively added 1 ml of acetone, 1 ml of methanol and 10 ml of ethyl acetate, until the aluminium salts precipitate. After filtering and washing the precipitate with ether, the organic phase is evaporated. The residue is chromatographed on a silica column (eluent: ether-hexane 30/70) and 1.80 g of the expected compound is obtained. (Yield: 88%).

Melting point, (after crystallizing from ether), 84° C.
IR Spectrum (film): 3420-1680 cm⁻¹.
NMR ¹H spectrum (60 MHz, CDCl₃): 3.9 (m 1H) 2.6–1.7 (m 5H) 1.2 (s 3H) 1.1 (s 3H) 1.05 (s 3H) 0.9 (s 3H).

EXAMPLE 2

Mesylate of tetramethyl-2,2,5,5-cyclohexanone-4-ol-1

0.4 ml of mesyl chloride is added to 600 mg of the compound obtained at example 1 and 1 ml of triethylamine in 7 ml of anhydrous methylene chloride, at 0° C., under agitation; the mixture is maintained for 30 minutes at this temperature, then hydrolysed with water and extracted with ether. The organic phase is washed with salt water, then dried and evaporated. After chromatographing on a silica column (eluent: ethyl acetate-hexane 40/60), 850 mg of the expected mesylate is obtained (yield 97%).

Melting point (after crystallizing from ether-hexane), 51° C.
IR spectrum (nujol): 1710 cm⁻¹.
NMR ¹H spectrum (60 MHz, CCl₄): 4.8 (dd J=6 8 Hz 1H) 3.0 (s 3H) 2.6–1.9 (m 4H) 1.2 (s 3H) 1.15 (s 3H) 1.10 (s 3H) 0.95 (s 3H).

EXAMPLE 3

Lactone of cis-dimethyl-2,2-(methyl-2'-propenyl-1')-3-cyclopropane-1-carboxylic acid Stage A: Lactone of trimethyl-3,3,6-hydroxy-6-mesyloxy-4-heptanoic acid 850 mg of mesylate obtained according to example 2 and 1 g of metachloroperbenzoic acid are agitated in 4 ml of anhydrous methylene chloride. After 100 hours, the solution is filtered, the precipitate is washed with methylene chloride, the organic phases are combined and then evaporated. After chromatographing on a silica column (eluent: ethyl acetatehexane 60/40), 766 mg of the expected product is obtained. (Yield 85%).

Melting point (after crystallizing from an ethyl acetate-ether mixture), 128° C.

IR Spectrum (Nujol): 1700 cm$^{-1}$.

NMR $^1$H Spectrum (60 MHz, CDCl$_3$): 4.8 (dd J=6 6 HZ 1H) 3.1 (s 3H) 2.75 (m 2H) 2.4 (m 2H) 1.6 (s 6H) 1.2 (s 3H) 1.1 (s 3H).

Stage B: Lactone of cis-dimethyl-2,2-(methyl-2'-propenyl-1')-3-cyclopropane-1-carboxylic acid or lactone of cis-chrysanthemic acid 1.15 ml of a 1.5M solution of sodium tert-amylate in benzene is added to 380 mg of the lactone mesylate obtained at Stage A in 4 ml of anhydrous tetrahydrofuran, at 0° C. The temperature is allowed to rise to 20° C. over 15 minutes. After hydrolysis, extraction is done with ether, then the organic phase is washed with salt water, dried and evaporated to dryness. After chromatographing on a silica column (eluent: ethyl acetate-hexane 40/60), 220 mg of the expected cis cyclopropane lactone is obtained. (Yield: 95%).

Melting point, 50.5° C.

Mass spectrum M/e=168 (M+) 153 124 109 95 81 67 55 43.

IR Spectrum (film): 1720 cm$^{-1}$.

NMR $^1$H Spectrum (400 MHz, CDCl$_3$): 1.92 (dd J=9.7 15.0 Hz 1H) 1.65 (dd J=5.1 15.0 1H) 1.55 (d J=7.7 Hz 1H) 1.44 (s 3H) 1.41 (ddd J=5.1 7.7 9.7 Hz 1H) 1.34 (s 3H) 1.22 (s 3H) 1.08 (s 3H).

Litt. H. Lehmkuhl, K. Mehler; Liebigs Ann. Chem 11, 1841, (1978).

Use of the lactone obtained in example 3 for the preparation of cis-chrysanthemic acid or racemic cis-dimethyl-2,2-(methyl-2'-propenyl-1')-3-cyclopropane-1-carboxylic acid 40 mg of the lactone obtained in the above example is heated in the presence of 146 mg of hexahydrated magnesium bromide in 0.25 ml of anhydrous pyridine at 125° C. for 14 hours. After acidifying with 0.5 ml of 5N hydrochloric acid, the aqueous phase is extracted with ether; the organic phases are combined, washed with dilute hydrochloric acid and then with salt water, then dried and evaporated to dryness. After chromatographing on a silica column (eluent: ethyl acetate-hexane 20/80), 35 mg of pure cis-chrysanthemic acid is isolated (Yield: 88%). The cis-chrysanthemic acid obtained is identical to an authentic sample described by J. Ficini, J. d'Angelo, Tetrahedron Letters (1976) 2441 and J. Ficini, S. Falou, J. d'Angelo, Tetrahedron Letters (1983) 375.

EXAMPLE 4

(+)-(S)-Tetramethyl-2,2,5,5-cyclohexanone-4-ol-1

*Curvularia lunata* NRRL2380, preserved on a solid medium[a] is seeded into a liquid medium[b] and cultivated for 48 hours at 24° C. in a rotary incubator. The diketone obtained at example 1 or 2 is added in solution at 5% in ethanol to a final concentration of 500 mg per liter of liquid medium. After three days of additional agitation at 24° C., chromatographing in a vapour phase of an extract obtained with ethyl acetate indicates 95% of conversion into ketol, which is isolated by filtration on celite, saturation of the filtrate with sodium chloride and repeated extraction with dichloromethane. After drying and evaporation. 460 mg of a pale yellow crystallized product is obtained. which is decolourized with active carbon and which is re-crystallized from hexane to obtain the (S) (+) ketol (252 mg). Treatment of the mother liquors enables about a further 100 mg of pure (S) ketol to be obtained. Yield: 70%.

Melting point (after crystallizing from ether): 103°–104° C.

IR Spectrum (Nujol): 3420–1680 cm$^{-1}$.

NMR $^1$H Spectrum (60 MHz. CDCl$_3$): 3.9 (m 1H) 2.6–1.7 (m 5H) 1.2 (s 3H) 1.1 (s 3H) 1.05 (s 3H) 0.9 (s 3H). [α]$_D^{20}$=89.7° (c=0.3 MeoH).

[a]Solid medium: Glucose, 20 g, peptone, 5 g, Bacto-Yeast Extract, 5 g, Bacto-Malt Extract, 5 g, Bacto-agar, 20 g, for one liter.
[b]Liquid medium (Nakazaki etal., J. Org. Chem., 44 (1979) 4588).

Chromatography in vapour phase of an isopropyl urethane derivative of the ketol on a chiral column (Rα-phenyl glycinamide) detects only one peak, which corresponds to the presence of a single stereo-isomer.

EXAMPLE 5

(+)-(S)-tetramethyl-2,2,5,5-cyclohexanone-4-ol-1

The results obtained by reducing the diketone of example 1 with different micro-organisms, operating at a diketone concentration of 1 g/l, are shown in the following table.

| Micro-organism | Reaction time | % of expected product (S) | % of diol formed | % of residual diketone. |
|---|---|---|---|---|
| Curvularia lunata NRRL 2380 | 75 H | 98.2 | — | 1.8 |
| Aspergillus niger | 48 H | 66.2 | 1 | 32.8 |
| Aspergillus ochraceus ATCC 1009 | 46 H | 89.2 | 10.8 | — |
| Mucor racemosus | 75 H | 85.2 | — | 14.8 |
| Geotrichum candidum | 119 H | 31.7 | — | 68.3 |
| Penicilium chrysogenum | 119 H | 69.9 | — | 30.1 |
| Rhizopus arrhizus ATCC 11145 | 119 H | 30.5 | — | 69.5 |

Numerous strains of the *Aspergillus niger, Mucor racemosus, Geotrichum candidum* and *Penicilium chrysogenum* species are easily available in various collections, notably in the ATCC or the NRRL.

EXAMPLE 6

Mesylate of (+)-(S) tetramethyl-2,2,5,5-cyclohexanone-4-ol-1

0,130 ml of mesyl chloride is added to 200 mg of the compound of example 4 and 0.33 ml of triethylamine in 3 ml of anhydrous methylene chloride, at 0° C., under agitation, and the mixture is maintained for 30 minutes at this temperature. After hydrolysis by the addition of 2 ml of water and extraction with ether, the organic phase is washed with 1 ml of salt water, then dried on MgSO$_4$ and evaporated. After chromatography on a silica column (eluent: ethyl acetate-hexane 40/60), 283 mg of the expected mesylate is obtained. (Yield: 97%).

Melting point (after crystallization from an ether-hexane mixture, 56°–57° C.

IR Spectrum (Nujol): 1710 cm$^{-1}$

NMR $^1$H Spectrum (60 MHz, CCl$_4$): 4.8 (dd J=6.8 Hz 1H) 3.0 (s 3H) 2.6–1.9 (m 4H) 1.2 (s 3H) 1.15 (s 3H) 1.10 (s 3H) 0.95 (s 3H).

$[\alpha]_D^{20} = +60.7°$ (c=2.06 CHCl$_3$)

EXAMPLE 7

LACTONE (+) of cis-dimethyl-2,2-(methyl-2'-propenyl-1')-3-cyclopropane-1-carboxylic acid Stage A: Lactone (+)-(S) of (S)-trimethyl-3,3,6-hydroxy-6-mesyloxy-4-heptanoic acid 283 mg of the mesylate obtained at example 6 and 0.33 g of metachloroperbenzoic acid are agitated in 2 ml of anhydrous methylene chloride. After 100 hours, the solution is filtered, the precipitate is washed with methylene chloride, and the organic phases are combined and then evaporated. After chromatographing on a silica column (eluent: ethyl acetate-hexane 60/40, 255 mg of the expected product is obtained. (Yield: 85%).

Melting point, (after crystallizing from an ethyl acetate-ether mixture), decomposition towards 100° C.

IR Spectrum (Nujol): 1700 cm$^{-1}$.

NMR $^1$H Spectrum (60 MHz, CDCl$_3$): 4.8 (dd J=6 Hz 1H) 3.1 (s 3H) 2.75 (m 2H) 2.4 (m 2H) 1.6 (s 6H) 1.2 (s 3H) 1.1 (s 3H).

$[\alpha]_D^{20} = +24.7°$ (c=1.9 CHCl$_3$).

Stage B: Lactone (+)-(1R,3S) of cis-dimethyl-2,2(methyl-2'-propenyl-1')-3-cyclopropane-1-carboxylic acid, or lactone (+) of (1R,3S) cis-chrysanthemic acid 0.38 ml of a 1.5M solution of sodium tert-amylate in benzene is added to 126 mg of the mesylate lactone obtained at stage A in 2 ml of anhydrous tetrahydrofuran, at 0° C. The temperature is allowed to rise to 20° C. over 15 minutes. After hydrolysis, extraction is done with ether, then the organic phase is washed with salt water. After chromatographing on a silica column (eluent acetate-hexane 40/60), 73 mg of the cis-cyclopropane lactone expected is obtained.

(Yield: 95%).

Melting point (after crystallizing from hexane) 83°–84° C.

Mass Spectrum M/e: 168 (M+) 153, 124, 109, 95, 81, 67, 55, 43.

IR Spectrum (film): 1720 cm$^{-1}$

NMR $^1$H Spectrum (400 MHz, CDCl$_3$): 1.92 (dd J=9.7; 15.0 Hz 1H) 1.65 (dd J=5.1; 15.0 Hz 1H) 1.55 (d J=7.7 Hz 1H) 1.44 (s 3H) 1.41 (ddd J=5.1; 7.7; 9.7 Hz 1H) 1.34 (s 3H) 1.22 (s 3H) 1.08 (s 3H).

$[\alpha]_D^{20} = +78°$ (c=1.2 in CHCl$_3$).

(Literature: S Torri, T. Inokuchi, R. Oi; J. Org. Chem. Vol 48, p. 1944 (1983): $[\alpha]_D^{22} = 77.6°$ (c=1.8 in CHCl$_3$).

m.p., 83° C.).

We claim:

1. A process for the preparation of a compound of the formula of cis structure

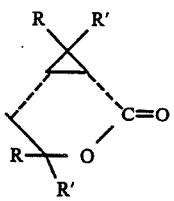

wherein R and R' are individually alkyl of 1 to 5 carbon atoms comprising alkylating cyclohexane-1,4-dione of the formula

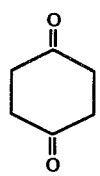

II to obtain 2,2,5,5-tetraalkyl-cyclohexane-1,4-dione of the formula

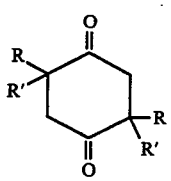

III selectively reducing the latter to obtain the corresponding 2,2,5,5-tetraalkyl-cyclohexan-4-one-1-ol of the formula

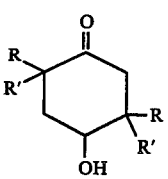

reacting the latter with a sulfonylating agent to obtain a compound of the formula

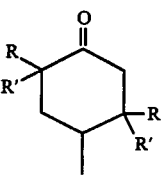

I' wherein R''' is selected from the group consisting of alkyl of 1 to 5 carbon atoms and aryl of 6 to 14 carbon atoms, oxidizing the latter with a peroxide to form a lactone of the formula

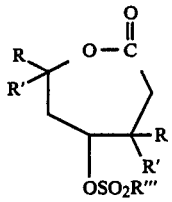

and subjecting the latter to cyclopropanation in a basic medium to obtain the cis form of the compound of formula V.

2. Process according to claim 1, characterized by the fact that the selective reduction stage includes the previous formation of a mono-enolate of the compound with the formula (III).

3. Process according to claim 2, characterized by the fact that the said mono-enolate is formed in the presence of an alkaline alcoholate in an anhydrous medium and at a temperature of about 0° C.

4. Process according to claim 1, characterized by the fact that the selective reduction is carried out by means of a hydride.

5. Process according to claim 4, characterized by the fact that the said hydride is diisobutylaluminium hydride or a borohydride such as sodium borohydride.

6. Process according to claim 1, characterized by the fact that at the sulphonylation stage, a halide of an alkyl- or aryl-sulphonic acid is used.

7. Process according to claim 6, characterized by the fact that the halide of an alkyl- or aryl-sulphonic acid is mesyl chloride or tosyl chloride.

8. A process according to claim 1, characterized by the fact that the peracid is metachloroperbenzoic acid.

9. A process according to claim 1, characterized by the fact that the cyclopropanating reaction is carried out in the presence of an alkaline alcoholate in an anhydrous medium, at a temperature of about 0° C.

10. A process according to claim 1, characterized by the fact that R and R' are identical and each represents a methyl radical.

* * * * *